United States Patent [19]

Fisher

[11] 4,210,052
[45] Jul. 1, 1980

[54] SCORING MECHANISM
[75] Inventor: Arnold R. Fisher, Laurinburg, N.C.
[73] Assignee: Libbey-Owens-Ford Company, Toledo, Ohio
[21] Appl. No.: 946,480
[22] Filed: Sep. 28, 1978

Related U.S. Application Data

[63] Continuation of Ser. No. 795,069, May 9, 1977, abandoned.

[51] Int. Cl.² ................................... B26D 3/08
[52] U.S. Cl. ................................ 83/881; 83/886
[58] Field of Search ............... 83/861, 879–886; 225/96.5

[56] References Cited
U.S. PATENT DOCUMENTS

| | | | |
|---|---|---|---|
| 2,948,991 | 8/1960 | Walters et al. | 225/96.5 |
| 4,070,936 | 1/1978 | Duncan | 83/861 |

*Primary Examiner*—J. M. Meister
*Attorney, Agent, or Firm*—Collins, Oberlin & Darr

[57] ABSTRACT

A method of and apparatus for precisely locating and quickly producing intermittent, uniform score lines in a surface of a moving sheet of material by first moving a pair of axially aligned gauge wheels into contact with the sheet material and then alternately moving a scoring tool positioned therebetween, into and out of scoring engagement with the surface of the moving sheet. The gauge wheels are mounted on the movable end of a pivotally mounted arm for movement, by a diaphragm motor, along a path lying in a plane extending normal to and longitudinally of the sheet material. The scoring tool is mounted on the arm for movement independent thereof by a double acting motor, and into and out of scoring contact with the sheet material. Also, the scoring tool is provided with an adjusting device for extending it relative to the gauge wheels and an abutment is provided to limit its movement away from the sheet material. This construction allows the scoring tool to be quickly moved into and out of engagement with the surface of the sheet material to precisely begin and end a score line and to produce a uniform score line by being urged into engagement therewith with a substantially constant force regardless of any variations occurring in the thickness of the sheet material.

5 Claims, 4 Drawing Figures

SCORING MECHANISM

This is a continuation of Ser. No. 795,069, filed May 9, 1977, now abandoned.

BACKGROUND OF THE INVENTION

1. Field of the Invention

This invention generally relates to mechanisms for scoring sheet material and more particularly to mechanisms for precisely producing intermittent, uniform score lines in the surface of a moving sheet of material.

2. Description of the Prior Art

In the manufacture of flat glass such as by the float process wherein a continuous ribbon of glass is produced, it is desirable to cut the cooled glass ribbon into sections of desired block sizes by a continuous operation in which the glass ribbon is both longitudinally and transversely scored; an example of such a scoring arrangement being shown in U.S. Pat. No. 3,439,849 issued on Apr. 22, 1969. In such a scoring arrangement, it is extremely important that the longitudinal score lines begin and end precisely at the location of the transverse score lines since, if they do not precisely intersect, curved corners may be formed when the scored sections of the glass ribbon are subsequently broken. For architectural glass cut to finished sizes, in particular, such corners are unacceptable.

The scoring tools normally employed in the above-described arrangement, particularly those producing longitudinally extending score lines, usually include a scoring wheel disposed between a pair of longitudinally aligned free running wheels which move into and out of engagement with the surface of the glass ribbon such as shown, for example, in U.S. Pat. No. 3,742,793, issued on July 3, 1973. Conventionally, such scoring tools are mounted on brackets or tracks for movement across the glass surface in such manners and in such positions that the glass ribbon will be both longitudinally and transversely scored as the glass ribbon moves therebeneath. Many attempts have been made to provide scoring mechanisms having a fast response wherein uniform longitudinal score lines precisely intersect the transverse score lines to form a square corner. However, since the means for moving the scoring tools also have had to move the above-described gauge wheels, such mechanisms have had a relatively slow response and the intersections of the longitudinal and transverse score lines have been irregular, thus resulting in curved corners when the sections are subsequently broken along these lines.

SUMMARY OF THE INVENTION

Briefly, the scoring mechanism constructed in accordance with this invention overcomes the aforementioned disadvantages by providing a scoring mechanism which is fast acting and precisely locates score lines in a sheet of moving material. The scoring tool thereof is provided with a small increment of movement and it moves independently of the gauge wheels which are urged with a constant pressure against the surface of the moving sheet of material. More specifically, the scoring mechanism generally comprises a scoring wheel that is connected to a piston rod of a double-acting cylinder mounted on a movable carrying arm having gauge wheels mounted thereon which are disposed on either side of the scoring wheel. The double-acting cylinder is provided with adjustable stop means for limiting upward movement of the scoring tool. Also, the connection between the scoring tool and the piston rod includes an adjusting device. The carrier arm is moved along a path lying in a plane extending normal to and longitudinally of the surface of the moving sheet of material by a single-acting diaphragm motor which urges the gauge wheels into contact with surface of the sheet material with a constant pressure.

OBJECTS AND ADVANTAGES

An object of this invention is to provide a scoring mechanism which has a fast and accurate response for producing precisely located intermittent longitudinally extending score lines in a moving ribbon of glass.

Another object of this invention is to provide a scoring mechanism wherein a scoring tool is pressed against the surface of a moving ribbon of glass with a substantially constant pressure under all operating conditions.

Yet another object of this invention is to provide a scoring mechanism which is simple in construction, and easily serviced and adjusted to provide optimum performance over extended periods of operation.

Other objects and advantages will become more apparent during the course of the following description when taken in connection with the accompanying drawings.

BRIEF DESCRIPTION OF THE DRAWINGS

In the drawings, wherein like numerals are employed to designate like parts throughout the same.

DESCRIPTION OF THE PREFERRED EMBODIMENT

Figure 1:
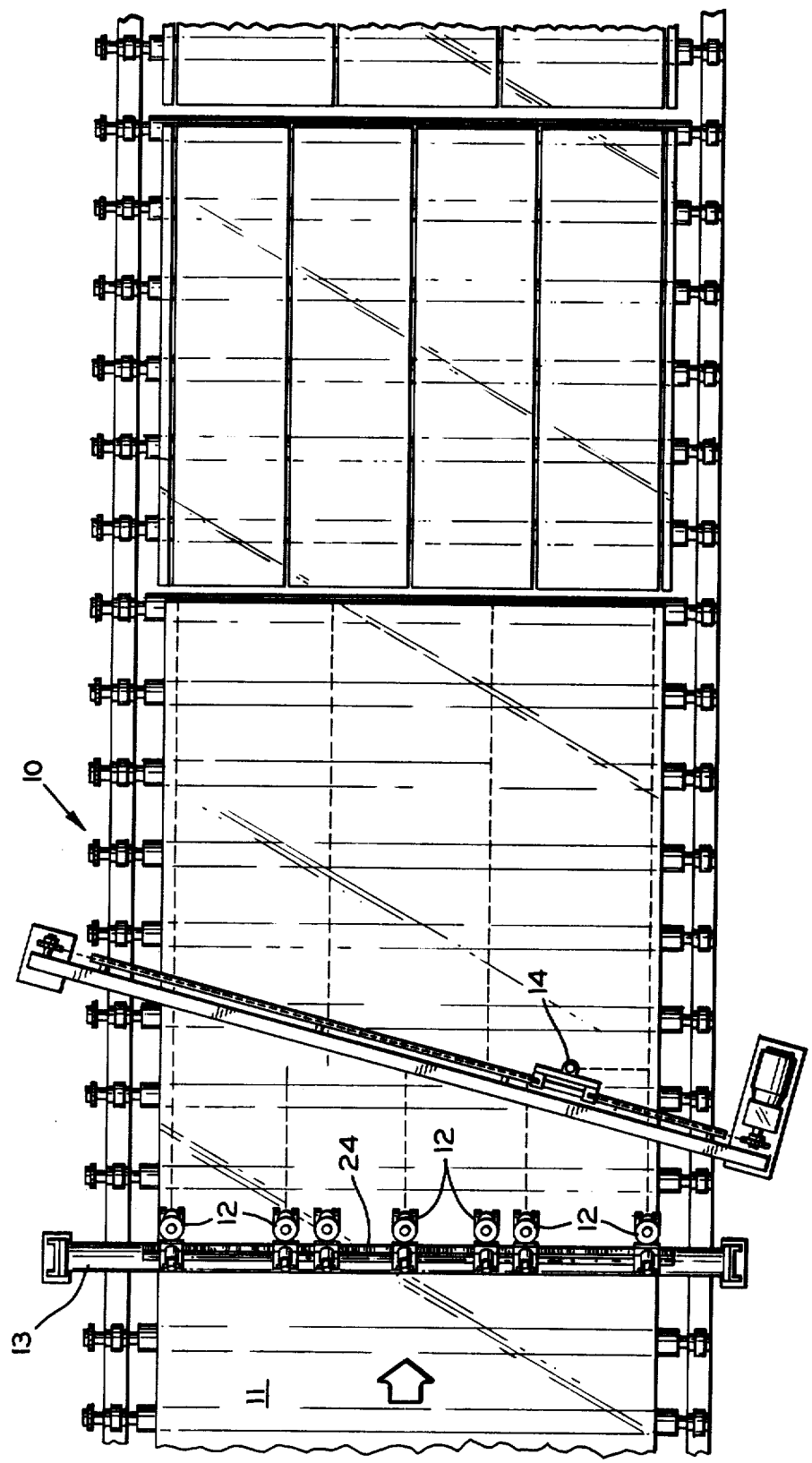
FIG. 1 is a diagrammatic view showing the arrangement of a plurality of scoring mechanisms for longitudinally and transversely scoring a moving ribbon of glass.

Referring now to FIG. 1, there is illustrated a driven conveyor 10 conveying a ribbon of glass 11 under a plurality of longitudinally oriented scoring mechanisms each designated in its entirety by the reference numeral 12, and each mounted on a fixed horizontal support bar 13. Each scoring mechanism 12 is shown to be positionable on the support bar 13 and once positioned, remains stationary while the glass ribbon 11 is conveyed therebeneath. Also illustrated is a conventional movable transverse scoring mechanism 14. Although each scoring mechanism 12 is ideally suited for producing longitudinally extending score lines in a moving glass ribbon, such mechanism also may be adapted for producing transversely extending score lines in glass ribbons or even for that matter in individual glass sheets.

Figure 2:
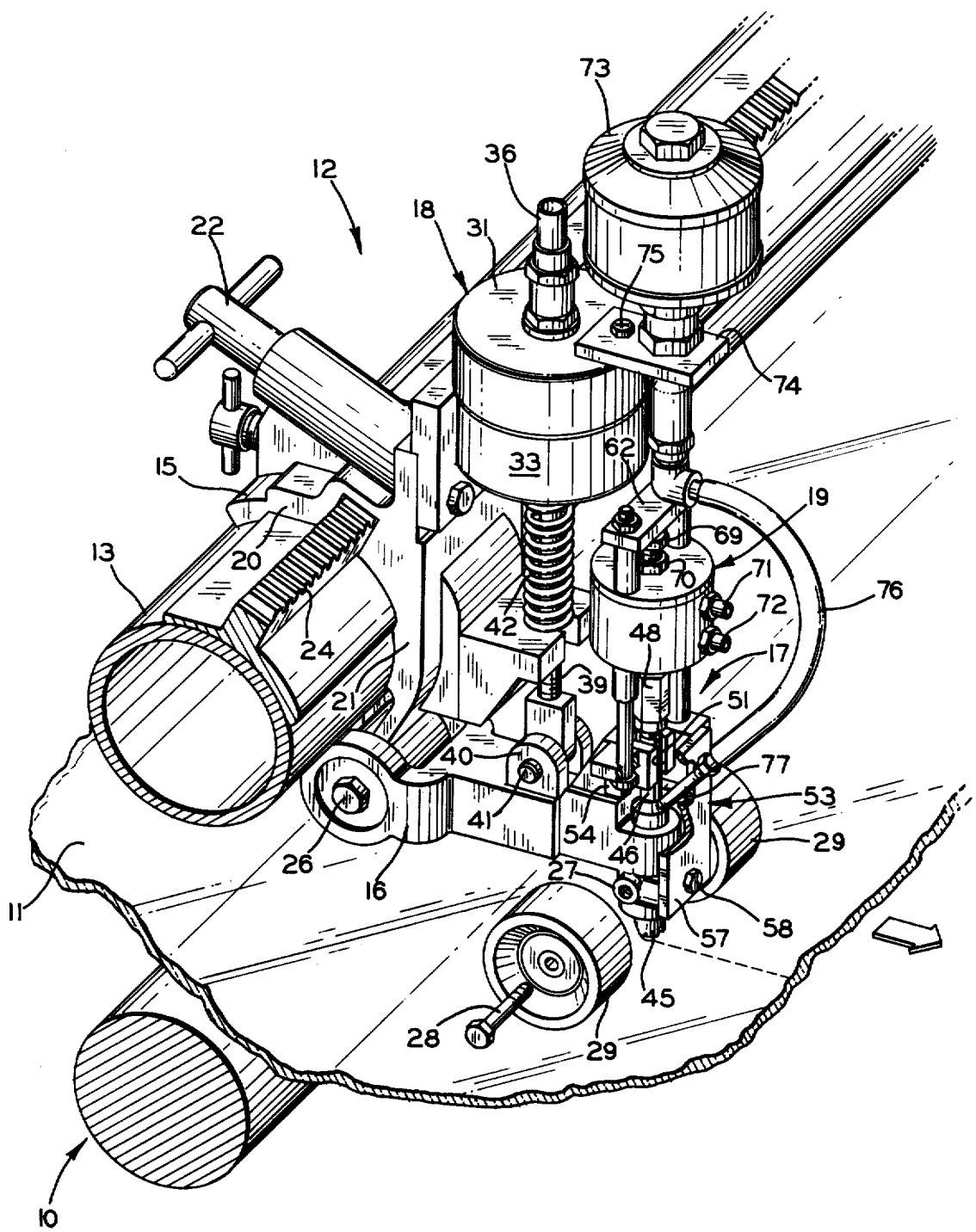
FIG. 2 is a perspective view of a glass scoring mechanism embodying the invention and employed in producing longitudinal scored lines in the glass ribbon illustrated in FIG. 1.

In accordance with the invention and as illustrated in FIG. 2, each scoring mechanism 12 generally comprises a mounting bracket 15 which is positionable along the support bar 13, a carrier arm 16 having one of its ends pivotally mounted on the bracket 15 so that its free end can be moved into contact with the glass ribbon 11 in a plane extending normal to and longitudinally of the top surface of the conveyed ribbon of glass 11 and a scoring device 17 which is supported on the free end of the carrier arm 16 for independent movement relative thereto. The scoring mechanism 12 also includes a pair of motors, one, a single acting diaphragm motor 18 for moving the carrier arm 16 along its path of travel and the other, a double-acting pancake-type motor 19 for moving the scoring device 17 into and out of contact with the top surface of the glass ribbon 11 independently of the movement of the carrier arm 16.

Figure 3:
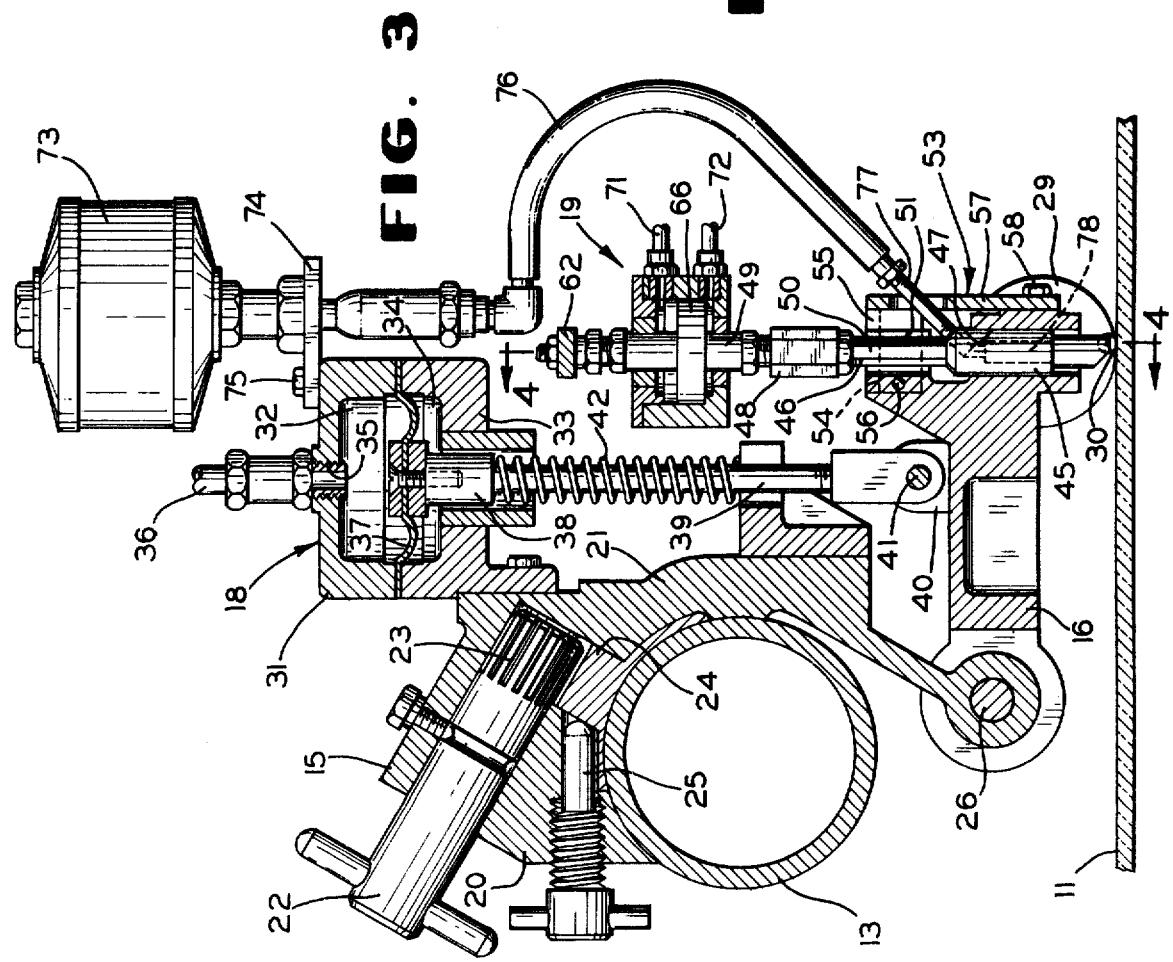
FIG. 3 is a side elevational view of a scoring mechanism illustrated in FIG. 2.

Referring now to FIG. 3, the mounting bracket 15 consists of an inverted generally L-shaped member having the inner surfaces of its upper horizontal leg 20 and its downwardly depending support leg 21 configured to seat on the horizontal support bar 13. Disposed within the horizontal leg 20 is a manually rotatable shaft 22 having a gear 23 at one end which engages a toothed rack 24 that is attached to the support bar 13. It will be observed that rotation of the gear 23 in the rack 24 in either direction will propel the bracket 15 along the bar 13 to a desired position. A locking pin 25 threaded within the horizontal leg 20 bears against the rack 24 to secure the bracket 15 in a fixed position on the bar 13. Hence, it may be seen that each scoring mechanism 12 is mounted on the support bar 13 so that it may be positioned along the length of the bar at any desired location.

Figure 4:
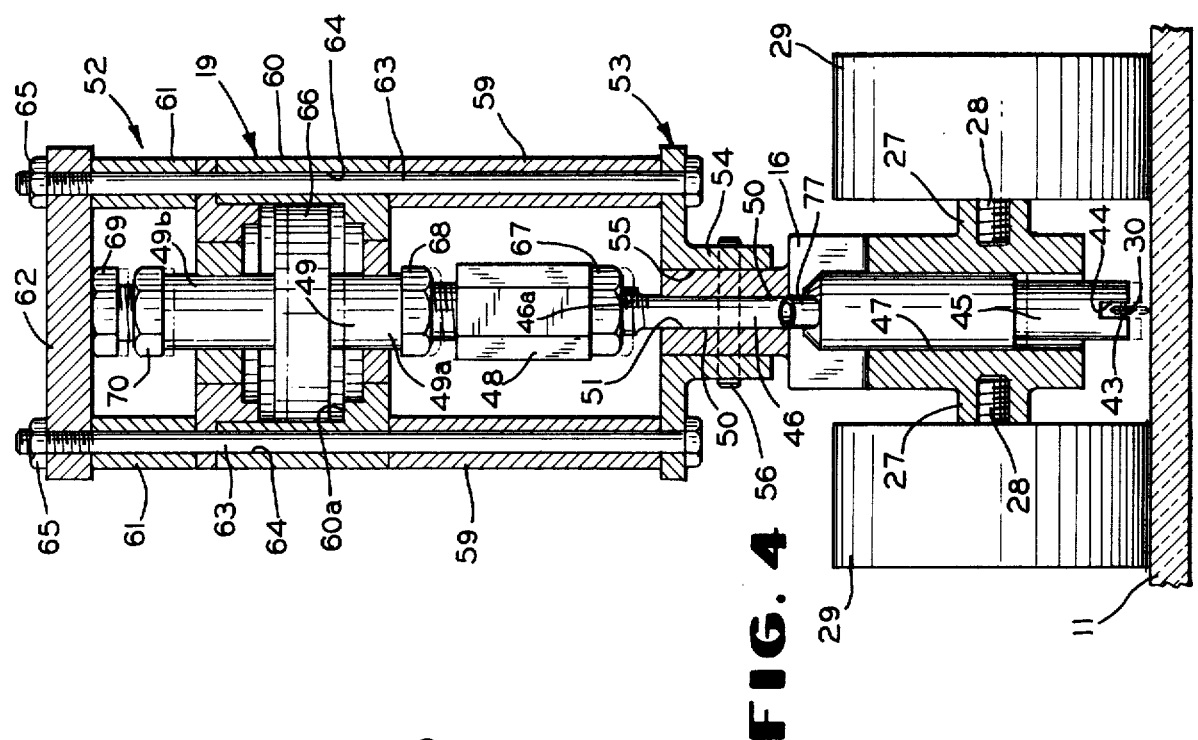
FIG. 4 is an enlarged cross-sectional view taken substantially along the line 4—4 of FIG. 3.

As illustrated in FIGS. 2 and 3, one end of the carrier arm 16 is pivotally attached to the end of the depending leg 21 of the bracket 15 by a pivot pin 26 so that its other end is movable in a plane extending normal to and longitudinally of the glass ribbon 11. Referring now to FIG. 4, the opposite sides of the carrier arm 16 adjacent its movable end are provided with hubs 27 for receiving axle bolts 28. The axle bolts support freely rotatable gauge wheels 29 which are positioned about the end of the carrier arm 16 so as to contact the surface of the glass ribbon 11 when the arm 16 is moved to its lower position.

As shown in FIGS. 2 and 3, the diaphragm motor 18 is supported by the bracket 15 and operatively connected to the carrier arm 16 to lower the gauge wheels 29 into contact with the surface of the glass ribbon 11 for supplying a proper pressure to a scoring wheel 30. More particularly, the diaphragm motor 18 includes a housing which is divided into two sections; the upper section 31 providing a fluid compression chamber 32 and the lower section 33 providing a chamber 34 vented to the atmosphere. The compression chamber 32 is provided with a tapped aperture 35 that is connected to a source of pressure (not shown) by a pressure line 36. A diaphragm 37 is secured in fluid tight relation between the upper and lower housing sections 31 and 33, respectively. A hub 38 attached to the central portion of the diaphragm 37 in a fluid tight relation connects one end of push rod 39 to the diaphragm 38 and its other end is connected to a clevis 40 disposed at the mid-portion of the carrier arm 16 by a pin 41 for moving the gauge wheels 29 into contact with the surface of the glass ribbon 11. A compression spring 42 surrounding the push rod 39 and supported between the bracket 15 and the diaphragm hub 38 urges the gauge wheels 29 out of contact with the glass ribbon 11.

As shown in FIGS. 3 and 4, the scoring device 17 includes the scoring wheel 30 which is rotatably mounted on an axle shaft 43. The axle shaft is horizontally disposed in a slot 44 formed in the head 45 of a reciprocally movable stem 46 which is connected to the motor 19. More specifically, the head 45 is disposed within an aperture 47 formed in the carrier arm 16 and is adapted to reciprocate therein. The stem 46, which is connected by a turnbuckle 48 to a piston rod 49 extending from the double-acting motor 19 to move longitudinally therewith, is held in proper operating position by having opposed flats 50 formed thereon contacting the sides of a U-shaped slot 51 formed in the carrier arm 16. The flats 50 permit longitudinal movement of the head 45 while preventing rotational movement thereof. The stem 46, and consequently the scoring wheel 30, is moved downwardly and upwardly relative to the carrier arm 16 by the double-acting motor 19 which is mounted on the movable end of the carrier arm 16.

As illustrated in FIG. 4, the double-acting motor 19 is mounted on the moving end of the carrier arm 16 by an open rectangular frame 52 which includes an angle-shaped bracket 53 attached to the carrier arm 16. More particularly and as best illustrated in FIG. 3, an upper horizontally extending leg 54 of the bracket 53 is provided with a U-shaped slot 55 whose inner sides contact the outer sides of that portion of the arm 16 in which the slot 51 is formed. A roll pin 56 extending through aligned apertures provided in the leg 54 and the arm 16 secures them together. A depending leg 57 of the bracket 53 is secured to the end of the arm 16 by a cap bolt 58. Referring now to FIG. 4, the motor 19 is longitudinally supported within the frame 52 and above the stem 46 by a pair of lower support tubes 59 which extend between a flange projecting from the leg 54 of the bracket 53 and the cylinder 60 of the motor 19. A pair of upper tubes 61 axially aligned with the lower support tubes 59 support a cross bar 62 which forms part of the frame 52 and also functions as an abutment for limiting upward travel of the cutting wheel 30 as will be described hereinafter. A pair of through bolts 63 extending upwardly from the bracket 53, through the tubes 59 and 61 and through apertures 64 provided in the cylinder 60, secure the motor 19 to the carrier arm 16 by means of nuts 65 threaded on the ends of the bolts 63 and engaging the cross bar 62.

The double-acting motor 19 is of conventional design and includes the cylinder 60 and the piston rod 49 which extends from each side of a piston 66 disposed within the cylinder 60. The lower portion 49a of the piston rod 49, as previously mentioned, is connected to the upper end of the stem 46, which is provided with external threads 46a, by the turnbuckle 48. A jam nut 67, provided on the threaded end of the stem 46, locks the stem to the turnbuckle. The upper end of the turnbuckle 48 is threaded to the lower portion of the piston rod 49 and a lock nut 68 secures the turnbuckle to the rod 49. Thus, rotation of the turnbuckle 48 moves the stem 46 relative to the motor 19 whereby the scoring wheel 30 may be adjusted to extend beyond the gauge wheels 29 so that score lines of a desired depth may be provided in the surface of the glass ribbon 11. The upper portion 49b of the piston rod 49 threadedly receives an adjustably positioned stop bolt 69 which is locked in a desired extension relative thereto by a jam nut 70. The stop bolt engages the cross bar 62 to limit upward movement of the piston 66 and consequently the uppermost position of the scoring wheel 30.

Referring now to FIG. 3, pressure lines 71 and 72 connect the cylinder 60 above and below the piston 66, respectively, with a source of pressurized air (not shown). Air may be admitted through either one of the lines at any desired time. For instance, if air is admitted to the cylinder 60 through the line 71 the piston 66 is forced to the bottom of the cylinder against a shoulder 60a, and the scoring wheel 30 is forced downwards onto the glass ribbon to the depth of its extended position beyond the gauge wheels 29. If, on the other hand, air is admitted through the line 72, the piston 66 is forced up the cylinder 60 and the scoring wheel 30 moves to a retracted position above the gauge wheels 29.

A lubricator 73 is mounted by means of a support plate 74 fixed to the upper housing section 31 of the diaphragm motor 18 by a cap screw 75. A lubricant or cutting oil is carried from the lubricator 73 by means of a flexible hose 76 which is connected to the head 45 supporting the scoring wheel 30 through a tube 77. A passageway 78 is provided in the head 45 so that the lubricant provides a film on the surface of the glass ribbon 11 to facilitate scoring of the surface by the wheel 30.

From the foregoing description, it is readily apparent that the scoring mechanism 12 can be operated to quickly respond and produce precisely located discontinuous or interrupted score lines; that is, score lines which commence and terminate at a position on the surface of the glass ribbon 11 which can be precisely intersected by transverse score lines. In this case, the gauge wheels 29 are first lowered into contact with the glass ribbon 11 and, once the gauge wheels are in operative position, only the scoring wheel 30 is extended or retracted to commence or terminate score lines at desired positions for producing block sizes of glass having sharp corners.

It is to be understood that the form of the invention herewith shown and described is to be taken as an illustrative embodiment only of the same, and that various changes in the shape, size and arrangement of the parts may be resorted to without departing from the spirit of the invention.

I claim:

1. In a scoring mechanism of the type mounted over a moving sheet of material and having an arm movable along a path lying in a plane extending normal to the surface and longitudinally along the path of the sheet material, the arm including a pair of axially aligned gauge wheels rotatably mounted thereon, the improvement comprising:
   a. means connected to said arm for moving and maintaining said gauge wheels in continuous rolling engagement with the moving sheet of material;
   b. a scoring tool mounted on said arm between said gauge wheels for movement relative thereto;
   c. means mounted on said arm and connected to said scoring tool, extending and retracting said scoring tool relative to said gauge wheels while the gauge wheels are maintained in continuous rolling engagement with the moving sheet of material whereby intermittent uniform score lines are precisely located and quickly produced in the moving sheet of material; and
   d. means connected between said scoring tool and said extending and retracting means for adjusting the extension of said scoring tool relative to said gauge wheels.

2. A scoring mechanism of the type mounted over a moving sheet of material as claimed in claim 1, wherein said means for moving and maintaining said gauge wheels in continuous engagement with the moving sheet of material comprises a single acting diaphragm motor.

3. A scoring mechanism of the type mounted over a moving sheet of material as claimed in claim 1, wherein said extending and retracting means connected to said scoring tool comprises a double-acting motor.

4. In a scoring mechanism of the type mounted over a moving sheet of material and having an arm movable along a path lying in a plane extending normal to the surface and longitudinally along the path of the sheet material, the arm including a pair of axially aligned gauge wheels rotatably mounted thereon, the improvement comprising:
   a. means connected to said arm for moving and maintaining said gauge wheels in continuous rolling engagement with the moving sheet of material;
   b. a scoring tool mounted on said arm between said gauge wheels for movement relative thereto;
   c. means mounted on said arm and connected to said scoring tool, extending and retracting said scoring tool relative to said gauge wheels while the gauge wheels are maintained in continuous rolling engagement with the moving sheet of material whereby intermittent uniform score lines are precisely located and quickly produced in the moving sheet of material; and
   d. means for adjusting the extension of said scoring tool relative to said gauge wheels, said adjusting means comprising a turnbuckle and a jam nut for locking said turnbuckle in adjusted position.

5. In a scoring mechanism of the type mounted over a moving sheet of material and having an arm movable along a path lying in a plane extending normal to the surface and longitudinally along the path of the sheet material, the arm including a pair of axially aligned gauge wheels rotatably mounted thereon, the improvement comprising:
   a. means connected to said arm for moving and maintaining said gauge wheels in continuous rolling engagement with the moving sheet of material;
   b. a scoring tool mounted on said arm between said gauge wheels for movement relative thereto; and
   c. means mounted on said arm and connected to said scoring tool, extending and retracting said scoring tool relative to said gauge wheels while the gauge wheels are maintained in continuous rolling engagement with the moving sheet of material whereby intermittent uniform score lines are precisely located and quickly produced in the moving sheet of material, said extending and retracting means comprising a double-acting motor, said double-acting motor including a piston having a double ended piston rod and said arm includes a stop plate for abutting one of said rod ends when said scoring tool is retracted from the surface of the moving sheet of material.

* * * * *